US009968894B2

(12) United States Patent
Shreve

(10) Patent No.: US 9,968,894 B2
(45) Date of Patent: May 15, 2018

(54) TARGETED FREQUENCY MULTIPLE PATH LENGTH MIXERS

(71) Applicant: Waters Technologies Corporation, Milford, MA (US)

(72) Inventor: Joshua Shreve, Franklin, MA (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 1004 days.

(21) Appl. No.: 14/362,750

(22) PCT Filed: Dec. 7, 2012

(86) PCT No.: PCT/US2012/068438
§ 371 (c)(1),
(2) Date: Jun. 4, 2014

(87) PCT Pub. No.: WO2013/090141
PCT Pub. Date: Jun. 20, 2013

(65) Prior Publication Data
US 2014/0334251 A1 Nov. 13, 2014

Related U.S. Application Data

(60) Provisional application No. 61/570,487, filed on Dec. 14, 2011.

(51) Int. Cl.
*B01F 1/00* (2006.01)
*B01F 5/06* (2006.01)
(Continued)

(52) U.S. Cl.
CPC .............. *B01F 5/06* (2013.01); *B01F 1/0005* (2013.01); *B01F 5/0644* (2013.01);
(Continued)

(58) Field of Classification Search
CPC ........ B01F 5/06; B01F 5/0601; B01F 5/0602; B01F 5/064; B01F 5/0644; B01F 13/0059;
(Continued)

(56) References Cited

U.S. PATENT DOCUMENTS 3,985,019 A 10/1976 Boehme et al.
4,767,279 A 8/1988 Dourdeville et al.
(Continued)

FOREIGN PATENT DOCUMENTS

EP 1193496 A1 4/2002
JP 5191175 A 8/1976
(Continued)

OTHER PUBLICATIONS

Publication by Noo Li Jeon et al; "Generation of Solution and Surface Gradients Using Microfluidic Systems", Langmuir 2000, vol. 16, pp. 8311-8316.*
(Continued)

*Primary Examiner* — Joseph Drodge
(74) *Attorney, Agent, or Firm* — Schmeiser, Olsen & Watts LLP

(57) ABSTRACT

Mixers in microfluidic separation systems comprise multiple fluidic paths that extend from a distribution well to a mixing well. An incoming flow of solvent composition splits at the distribution well into as many streams as fluidic paths. The streams recombine at the mixing well to produce an output stream. One embodiment has fluidic paths with different dwell volumes that determine a percentage of the incoming flow flowing through each path. These dwell volumes can be targeted to attenuate a known noise characteristic in the incoming compositional flow. Another embodiment of mixer has a contoured surface disposed between the distribution and mixing wells. The paths extend from the distribution
(Continued)

well to the mixing well through this contoured surface, each path passing through a different valley defined by opposing upwardly sloping banks. The valleys can have different dwell volumes that determine a percentage of the incoming compositional flow flowing through each valley.

28 Claims, 10 Drawing Sheets

(51) Int. Cl.
- B01F 15/04 (2006.01)
- G01N 30/04 (2006.01)
- B01F 13/00 (2006.01)
- G01N 30/34 (2006.01)
- B01D 15/16 (2006.01)
- G01N 30/60 (2006.01)

(52) U.S. Cl.
CPC ......... *B01F 13/0059* (2013.01); *G01N 30/04* (2013.01); *G01N 30/34* (2013.01); *B01D 15/16* (2013.01); *G01N 30/6095* (2013.01); *G01N 2030/347* (2013.01)

(58) Field of Classification Search
CPC .............. B01F 13/0061; B01F 13/0064; B01F 13/0066; B01F 15/04; B01F 15/0404; B01F 15/0412; B01F 15/0416; B01F 2215/0037; B01F 1/00; B01F 1/0005; B01F 1/0022; B01F 1/0038; B01F 5/0641; B01D 15/14; B01D 15/16; B01D 15/166; B01D 15/168; G01N 30/04; G01N 30/34; G01N 30/6095; G01N 2030/347
USPC ........ 210/198.2, 656, 659; 366/160.2, 160.3, 366/182.1, 336–341, 248; 417/313; 422/70

See application file for complete search history.

(56) References Cited

U.S. PATENT DOCUMENTS

| | | | |
|---|---|---|---|
| 6,887,384 B1 | 5/2005 | Frechet et al. | |
| 6,890,093 B2 | 5/2005 | Karp et al. | |
| 6,893,547 B2 | 5/2005 | Gascoyne et al. | |
| 7,134,453 B2 | 11/2006 | Peters et al. | |
| 7,143,785 B2 | 12/2006 | Maerkl et al. | |
| 7,261,812 B1* | 8/2007 | Karp .................. | B01D 15/1864 210/198.2 |
| 7,314,070 B2 | 1/2008 | Jeon et al. | |
| 2002/0113095 A1* | 8/2002 | Jeon ..................... | B01F 5/0601 222/424.5 |
| 2002/0134143 A1 | 9/2002 | Allington et al. | |
| 2007/0113907 A1 | 5/2007 | Brennen et al. | |
| 2007/0240989 A1 | 10/2007 | Levitan et al. | |
| 2007/0263477 A1* | 11/2007 | Sudarsan .............. | B01F 5/0644 366/3 |
| 2007/0269894 A1* | 11/2007 | Howland ............. | B01F 1/0022 436/50 |
| 2008/0043570 A1* | 2/2008 | Arnold .................. | B01F 5/0256 366/342 |
| 2009/0044619 A1* | 2/2009 | Fiering ................ | B01F 5/0641 73/202 |
| 2009/0148858 A1* | 6/2009 | Patel ................... | B01L 3/50273 435/7.1 |
| 2010/0040483 A1 | 2/2010 | Berger et al. | |
| 2010/0078086 A1 | 4/2010 | Guidat et al. | |
| 2011/0192217 A1 | 8/2011 | Choikhet et al. | |

FOREIGN PATENT DOCUMENTS

| | | |
|---|---|---|
| JP | 6248428 U | 3/1987 |
| JP | 6295727 U | 6/1987 |
| JP | 2005-211857 A | 8/2005 |
| JP | 2007090262 A | 4/2007 |
| JP | 4043718 B2 | 2/2008 |
| JP | 2009208052 A | 9/2009 |
| JP | 2010082533 A | 4/2010 |
| WO | 2010030720 A1 | 3/2010 |

OTHER PUBLICATIONS

International Preliminary Report on Patentability in counterpart international application No. PCT/US12/68438, dated Jun. 26, 2014; 6 pages.

Extended European Search Report in counterpart European patent application No. 128576853.7, dated Oct. 2, 2015; 7 pg.

Second Official Action in counterpart Japanese Patent Application No. 2014-547315, dated Feb. 14, 2017; 9 pages.

International Search Report & Written Opinion in International Patent Application No. PCT/US12/68438, dated Feb. 28, 2013; 7 pages.

Notice of Rejection in counterpart Japanese patent application No. 2014-547315, dated Aug. 30, 2016; 9 pages.

* cited by examiner

TARGETED FREQUENCY MULTIPLE PATH LENGTH MIXERS

RELATED APPLICATION

This application claims the benefit of and priority to co-pending U.S. provisional application No. 61/570,487, filed Dec. 14, 2011, titled "Targeted Frequency Multiple Path Length Mixers," the entirety of which is incorporated by reference herein.

FIELD OF THE INVENTION

The invention relates generally to microfluidic separation systems. More specifically, the invention relates to multi-path mixers used in microfluidic separation systems to mix solvent compositions.

BACKGROUND

Chromatography is a set of techniques for separating a mixture into its constituents. Generally, in a liquid chromatography analysis, a pump takes in and delivers a composition of liquid solvents at high pressure to a sample manager, where a sample (i.e., material under analysis) awaits injection into the mixture. Disposed between the pump and sample manager, a mixer blends the liquid solvents into a homogenous composition. From the sample manager, the resulting composition comprised of the mixture of liquid solvents and injected sample moves to a point of use, such as a column of particulate matter. By passing the composition through the column, the various components in the sample separate from each other at different rates and thus elute from the column at different times. A detector receives the elution from the column and produces an output from which the identity and quantity of the analytes may be determined High-performance liquid chromatography (HPLC) uses two basic elution modes: isocratic elution and gradient elution. In the isocratic elution mode, the mobile phase, comprised of either a pure solvent or a mixture of solvents, remains the same throughout the chromatography run. In the gradient elution mode, the composition of the mobile phase changes during the separation. Creation of the gradient involves the mixing of multiple solvents, the proportions of which change over time in accordance with a predetermined timetable. Some HPLC systems create the gradient under high pressure, by mixing the solvents downstream, on the outlet side of the pumps. Such HPLC systems are referred to herein as high-pressure gradient systems. Other HPLC systems create the gradient under low pressure, using a gradient proportioning valve to select from up to four solvents, combining the multiple solvents on the intake side of a single aspirating pump, and changing the proportions of the solvents over time. Such HPLC systems are referred to herein as low-pressure gradient systems.

The choice between a high-pressure and a low-pressure gradient system involves a variety of tradeoffs. For one, high-pressure gradient systems have lesser dwell volumes than low-pressure gradient systems because the solvent mixing occurs after the pumps instead of before the intake side of the pump. On the other hand, low-pressure gradient systems can produce a gradient with just one pump, whereas high-pressure gradient systems generally require one pump for each solvent. Hence, low-pressure-gradient systems are more amenable than high-pressure gradient systems to tertiary and quaternary gradients, and, thus, find use predominantly in such chromatography applications, whereas high-pressure gradient systems generally involve binary gradients.

The output stream of solvent composition produced by low-pressure and high-pressure gradient systems typically has detectable perturbations in a chromatographic baseline, referred to as compositional noise. When a gradient pump outputs a mixture of two fluids, frequencies of operation manifest as oscillations in the compositional output.

A conventional approach for reducing compositional noise is to couple a large-volume mixer to the output of the pump system. This mixer, however, may add an undesirable amount of delay volume to the chromatography system, which can affect the delivery of accurate and reproducible gradients and negatively affect cycle time for a liquid chromatography system. Furthermore, the mixer may actually be ineffective in adequately reducing the compositional noise.

SUMMARY

In one aspect, the invention features a mixer for use in a microfluidic separation system, comprising: a mixing well, a distribution well for receiving an incoming flow of solvent composition having a known noise characteristic, and a plurality of fluidic paths extending from the distribution well to the mixing well. The flow of solvent composition splits at the distribution well into as many streams as fluidic paths. The fluidic paths have different dwell volumes that determine a percentage of the flow of solvent composition carried by each of the fluidic paths. The dwell volumes of the fluidic paths are specifically configured to target the known noise characteristic in the flow of solvent composition. The streams recombine at the mixing well in accordance with the percentages determined by the dwell volumes of the fluidic paths to produce an output compositional stream having the noise characteristic attenuated.

In another aspect, the invention features a microfluidic separation system comprising a pump system pumping a flow of solvent composition with a known noise characteristic, and a mixer with a mixing well, a distribution well for receiving the flow of solvent composition having the known noise characteristic, and a plurality of fluidic paths extending from the distribution well to the mixing well. The flow of solvent composition splits at the distribution well into as many streams as fluidic paths. The fluidic paths have different dwell volumes that determine a percentage of the flow of solvent composition carried by each of the fluidic paths. The dwell volumes of the fluidic paths are specifically configured to target the known noise characteristic in the flow of solvent composition. The streams recombine at the mixing well in accordance with the percentages determined by the dwell volumes of the fluidic paths to produce an output compositional stream having the noise characteristic attenuated.

In still another aspect, the invention features a mixer for use in a microfluidic separation system. The mixer comprises a mixing well, a distribution well for receiving an incoming flow of solvent composition, and a contoured surface disposed between the distribution and mixing wells. The contoured surface has a plurality of fluidic paths extending from the distribution well to the mixing well. Each fluidic path passes through a different valley defined by opposing upwardly sloping banks. The incoming flow of solvent composition splits at the distribution well into as many streams as fluidic paths. The streams recombine at the mixing well to produce an output compositional stream.

In still another aspect, the invention features a microfluidic separation system comprising a pump system pumping a flow of solvent composition, and a mixer with a distribution well for receiving the flow of solvent composition, a mixing well, and a contoured surface disposed between the distribution and mixing wells. The contoured surface has a plurality of fluidic paths extending from the distribution well to the mixing well. Each fluidic path passes through a different valley defined by opposing upwardly sloping banks. The incoming flow of solvent composition splits at the distribution well into as many streams as fluidic paths. The streams recombine at the mixing well to produce an output compositional stream.

BRIEF DESCRIPTION OF THE DRAWINGS

The above and further advantages of this invention may be better understood by referring to the following description in conjunction with the accompanying drawings, in which like numerals indicate like structural elements and features in various figures. The drawings are not necessarily to scale, emphasis instead being placed upon illustrating the principles of the invention.

DETAILED DESCRIPTION

Microfluidic mixers described herein can be configured to target, for attenuation, specific frequencies or bands of frequencies in the solvent compositional stream produced by a pump coupled (upstream) to the intake port of the mixer. When a pump operates to output a mixture of two or more fluids, these frequencies of operation appear as perturbations or oscillations in the composition of the fluidic output of the pump. Such oscillations are referred to as compositional noise or error. This noise may originate from a variety of sources, including, but not limited to, mechanical features of the pump, such as motor resonances, ball and screw drives, gears, and/or other components to produce the linear motion that drives the pump piston(s). Other sources of noise include physical phenomena, such as stroke/refill periods, the onset or completion of solvent compression, or the onset of solvent delivery from the pump chamber.

The mixers perform like band stop filters by attenuating those frequencies in a specific range, while allowing other frequencies to pass through unaffected. To achieve the band stop filter-like behavior, a mixer has multiple paths or channels that split the incoming solvent compositional stream into multiple smaller streams. The dwell volume of each path determines the percentage of the incoming solvent compositional stream flowing through each of the paths. The mixer uses specific path geometries to configure the dwell volume of each path. Factors that determine the dwell volume of a given path include the path's length and flow resistance. Factors influencing flow resistance are the path's cross-sectional shape and cross-sectional area. (In general, the flow rate for any path is the product of its length and flow resistance.) The multiple streams recombine in accordance with their respective dwell volumes to attenuate or cancel the targeted periodic error in the output solvent compositional stream.

The multiple paths of the mixer can be discrete (i.e., separate from and independent of each other) or be embodied within a contoured surface, the contour of which is designed to control the mixing characteristics in order to attenuate compositional noise of known volumetric frequencies. In addition, the various embodiments of mixers described herein can be coupled to any type of pump. In general, the volumetric noise frequency of low-pressure gradient pump systems is a known parameter, and the design of a mixer can target this frequency. For high-pressure gradient pump systems, certain specific volumetric noise frequencies can be produced deliberately, for example, by varying the pump stroke lengths. The design of a mixer, for example, the number of paths and the geometry of each path, can specifically target these noise frequencies for attenuation.

Figure 1:
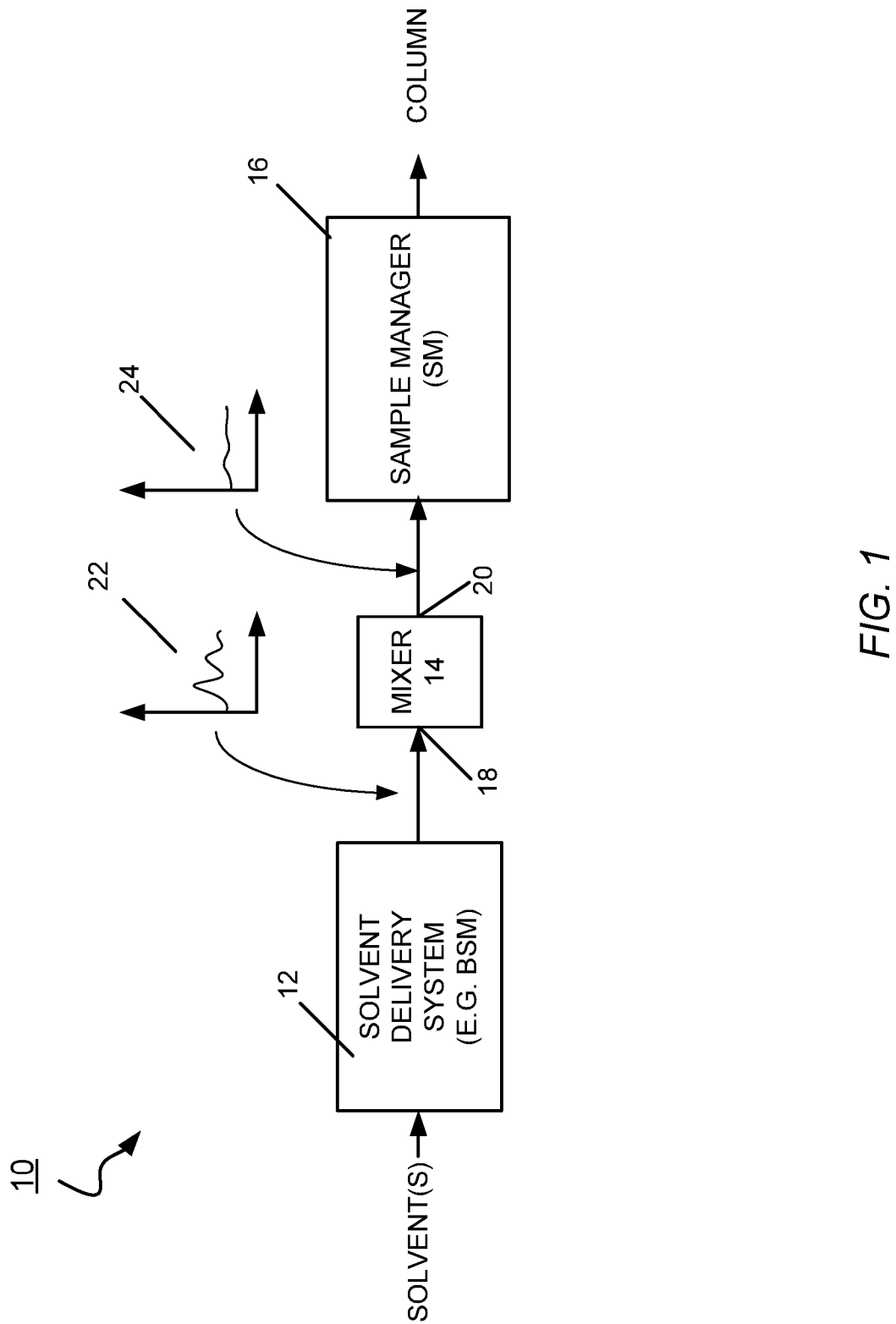
FIG. 1 is a functional block diagram of an embodiment of a liquid chromatography system having pump in communication with a multi-path mixer.

FIG. 1 shows an embodiment of a portion of a liquid chromatography (LC) system 10, for separating a sample into its constituents. The liquid chromatography system 10 includes a solvent delivery system 12, a multi-path mixer 14, and a sample manager 16. Generally, the solvent delivery system 12 includes one or more pumps (not shown) in fluidic communication with solvent reservoirs from which solvents are drawn. The solvent delivery system 12 can be implemented as a low-pressure gradient system with a gradient proportioning valve and a single pump delivering a solvent stream composed of multiple solvents. Alternatively, the solvent delivery system 12 can be a high-pressure gradient system with two pumps joined by a 'T' at their outlets, each pump delivering a single solvent. The intake port 18 of the mixer 14 is in fluidic communication with the solvent delivery system 12 to receive the solvent compositional stream; the outlet port 20 of the mixer 14 is in fluidic communication with the sample manager 16.

During operation, the solvent delivery system 12 delivers a solvent compositional stream to the mixer 14. The solvent compositional stream arriving at the mixer 14 has a compositional noise pattern as illustrated by graph 22. The multi-path mixer 14 mixes the solvents in the incoming solvent compositional stream in a manner that targets the compositional noise pattern for attenuation. Embodiments of the mixer 14 include discrete path mixers and contoured surface mixers as described in more detail below.

From the mixer 14, the filtered solvent compositional stream passes to the sample manager 16. The filtered solvent compositional stream has a reduced compositional noise pattern as illustrated by graph 24. The sample manager 16 is in fluidic communication with a sample source from which the sample manager acquires and introduces a sample to the solvent composition arriving from the mixer 14. From the sample manager 16, the solvent compositional stream, which includes the injected sample, passes to a chromatographic column. Embodiments of the liquid chromatography system 10 include HPLC and UPLC (Ultra Performance Liquid Chromatography) systems.

Figure 2:
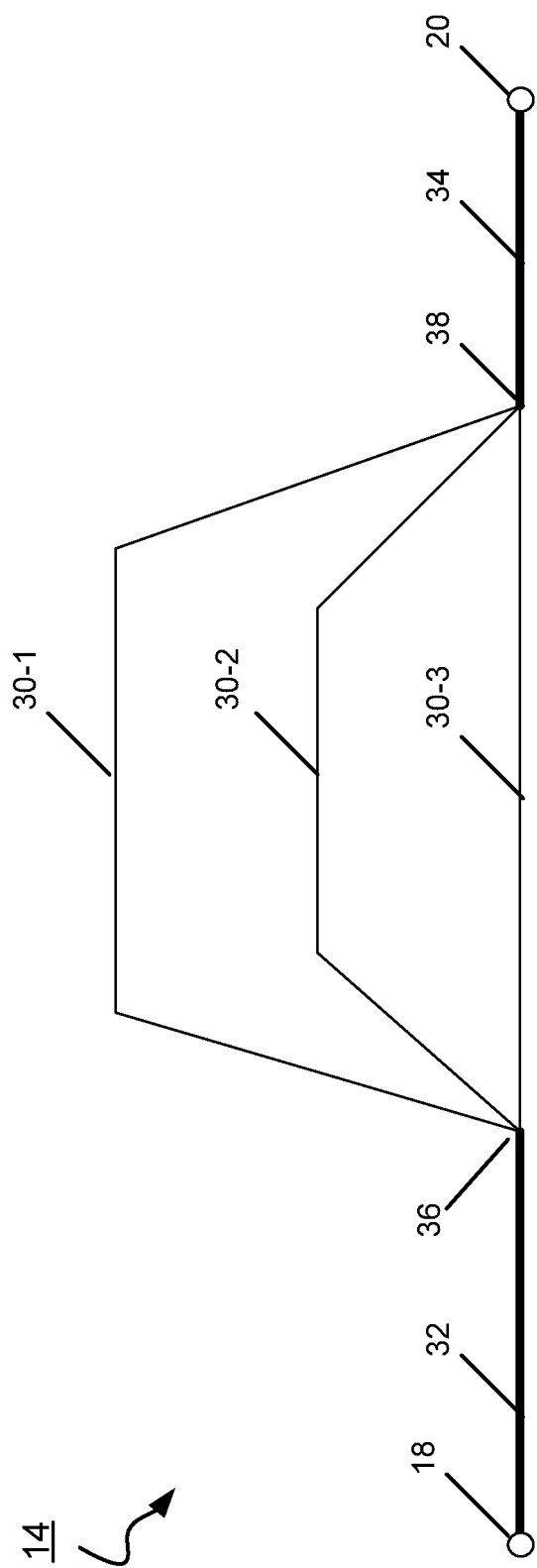
FIG. 2 is a diagram of one embodiment of the multi-path mixer, referred to as a discrete path mixer.

FIG. 2 shows an example embodiment of the multi-path mixer 14 having multiple discrete microfluidic paths 30-1, 30-2, and 30-3 (generally, 30) by which a compositional stream arriving at the intake port 18 can pass to the outlet port 20. An inlet channel 32 extends from the intake port 18 to the distribution well 36. An outlet channel 34 extends from a mixing well 38 to the outlet port 20. Each path 30 starts at the distribution well 36 and ends at the mixing well 38. In this example, path 30-1 is the longest of the three paths 30, and path 30-3 is the shortest, being a straight path between the distribution well 36 and mixing well 38. In FIG. 2, the thicknesses of the lines represent the relative cross-sectional areas of the paths: each of the inlet and outlet channels 32, 34 having greater cross-sectional areas than the paths 30. Each path 30 has a different dwell volume (here, in this example, more by virtue of their different lengths than of their cross-sectional areas, which are shown to be generally equal). The different dwell volumes cause the paths to carry different percentages of an incoming solvent compositional stream.

In brief overview, the incoming compositional stream enters the intake port 18, travels the inlet channel 32, and, at the distribution well 36, splits into three streams corresponding to the three paths 30. By virtue of their different dwell volumes, each path delivers a different percentage of the incoming compositional stream to the mixing well 38, where the streams recombine and mix to produce an output compositional stream without a specifically targeted periodic error. The output compositional stream leaves the mixer through the outlet port 20.

Figure 3:
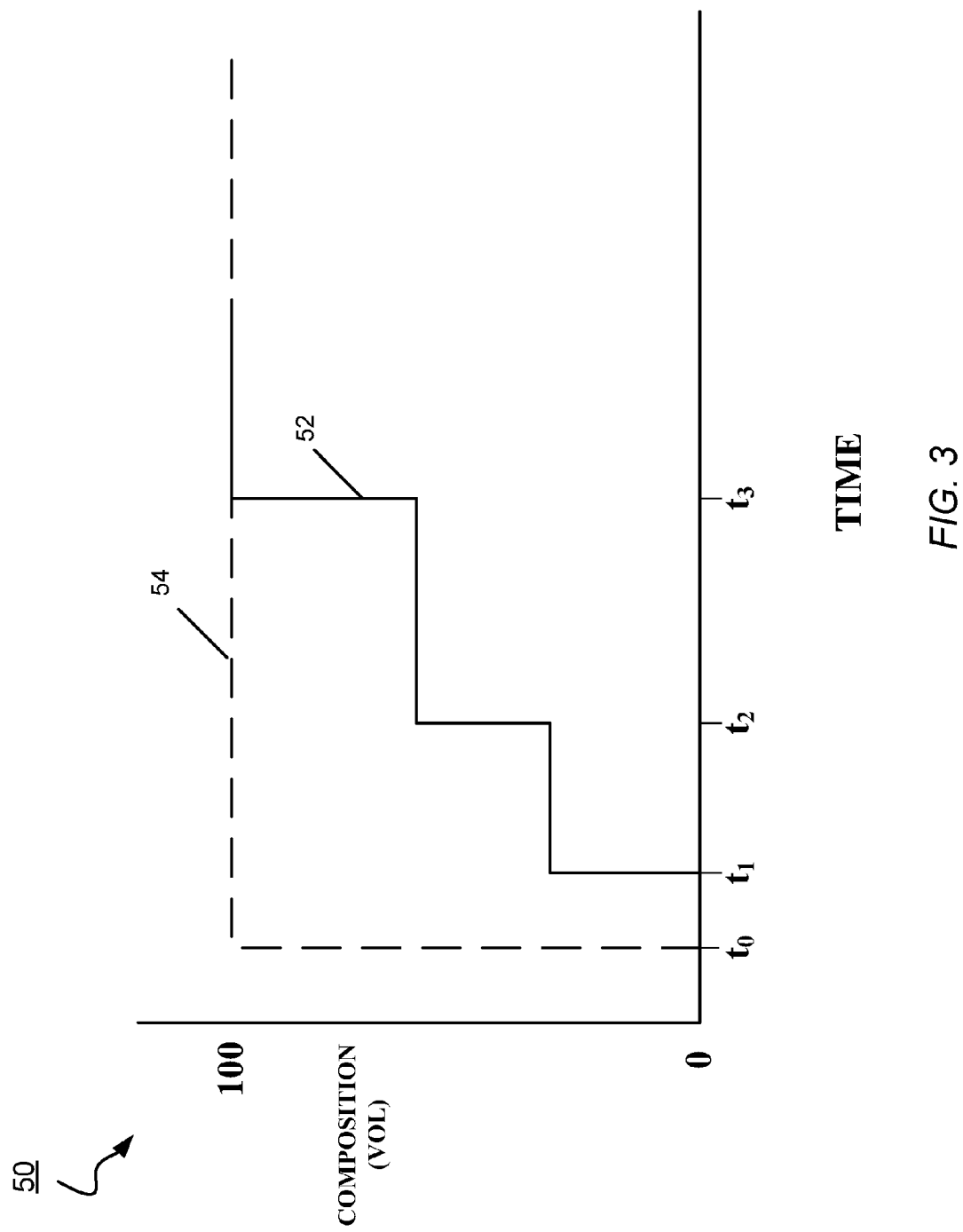
FIG. 3 is a plot showing an example of a mixer output over time in response to a step of composition sent through the mixer.

FIG. 3 shows a plot 50 of an example mixer output 52 produced the three-path mixer 14 of FIG. 2 in response to a step of composition sent through the mixer 14. A step of composition has a set volume, instead of being a continuous stream, and is being used here to illustrate the effect of dwell volume on travel time through the mixer 14. In general, a step of composition sent through the mixer 14 emerges as several smaller steps. At time t0, the mixer input 54 (represented by a step from 0 to 100) enters the mixer 14. Within the mixer, the input compositional step divides into three step portions over the three paths: the shortest path 30-3, the intermediate path 30-2, and the longest path 30-1.

At time t1, the portion of the compositional step that traverses the shortest path 30-3 is the first of the three to arrive at the mixing well 38. (For the purpose of this example, the paths have the same flow resistance and the path lengths determine travel time through each path). The volume at the mixer output 52 steps up according to the volume carried by that path 30-3. At time t2, the portion of the compositional step traversing the intermediate path 30-2 reaches the mixing well 38, where its volume adds to the volume arriving over the shortest path 30-3. The combined volume of the shortest and intermediate paths 30-3, 30-2 produces another step in mixer output volume. At time t3, the portion of the compositional step traversing the longest path 30-1 reaches the mixing well 38, where its volume adds to the combined volumes arriving over the shortest and intermediate paths 30-3, 30-2. The entirety of the mixer input 54 has emerged as mixer output 52.

Figure 4:
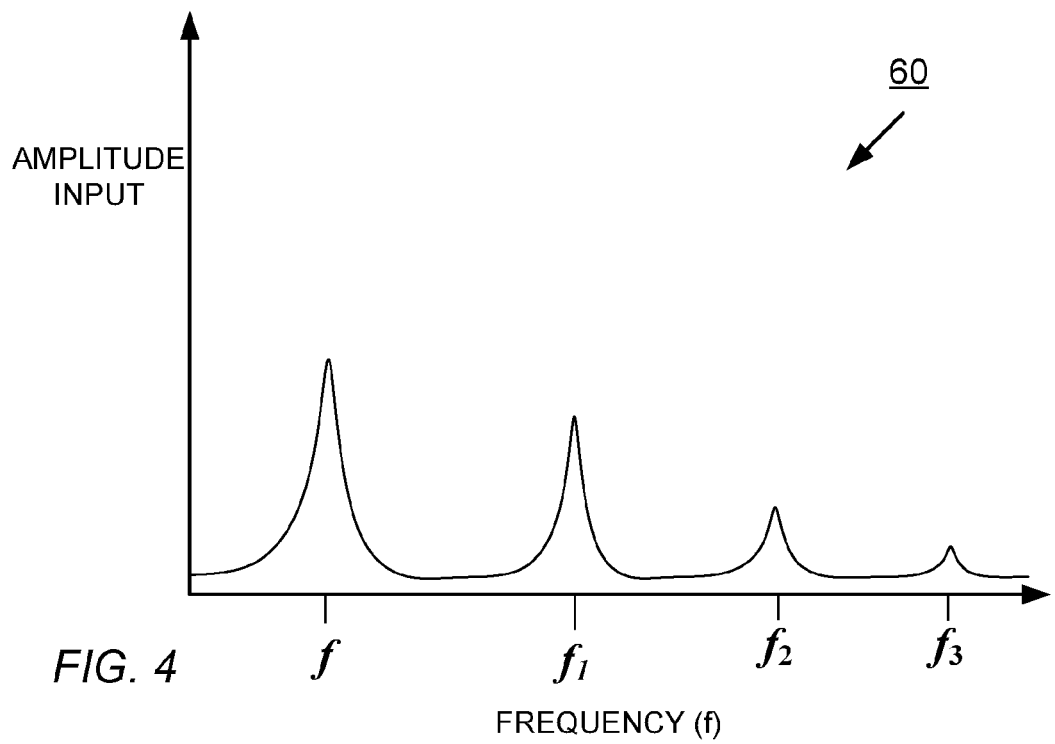
FIG. 4 is a frequency domain plot showing an example of a noise characteristic in a solvent compositional stream supplied to the mixer.

FIG. 4 shows a frequency-domain plot 60 of an incoming compositional stream, provided by the solvent delivery system 12 (FIG. 1) as input to the mixer 14, decomposed into its constituent frequencies. On the x-axis are the constituent frequencies, and on the y-axis are the amplitudes at these frequencies. In this example, the incoming compositional stream manifests a component frequency, f, and harmonic frequencies, $f_1$, $f_2$, and $f_3$, of decreasing amplitude. The plot 60 provides an example of periodic error in the incoming compositional stream, and can represent a noise profile to be targeted for attenuation or cancelation by the mixer 14.

Figure 5:
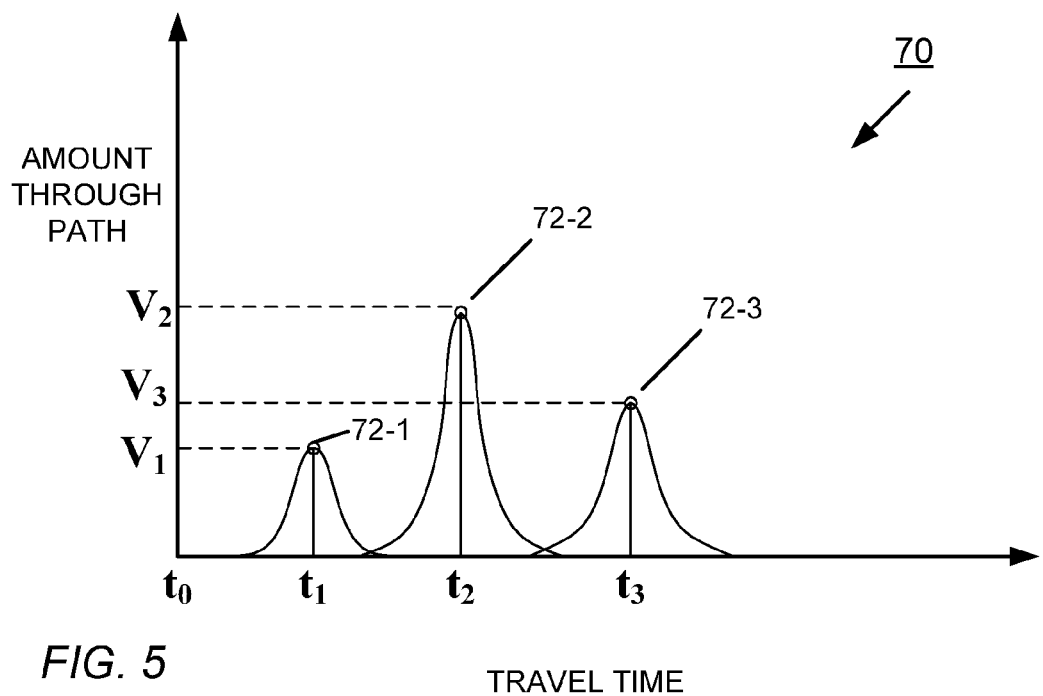
FIG. 5 is a plot of example travel time for the different paths of the multi-path mixer.

FIG. 5 shows a plot 70 with three example mixer output steps 72-1, 72-2, and 72-3 (generally 72) designed to produce a mixing profile that targets a specific noise profile, for example, the noise profile of FIG. 4. The x-axis represents the amount of travel time for portions of a compositional step to flow through the mixer 14. The y-axis represents the amount (volume) of compositional output by the mixer. The mixer 14 has three paths 30-1, 30-2, 30-2 that can be designed to produce these output steps so that certain percentages of the input compositional step emerge at the mixing well 38 in accordance with predetermined travel times. For example, the design of the geometries of path 30-1 can aim to deliver volume $V_1$ to the mixing well at time $t_1$; those of path 30-2, to deliver volume $V_2$ at time $t_2$; and those of path 30-3, to deliver volume $V_3$ at time $t_3$. A Bell curve represents each step 72 to show that each portion of the input compositional step arrives at the mixer output over a window of time.

Figure 6:
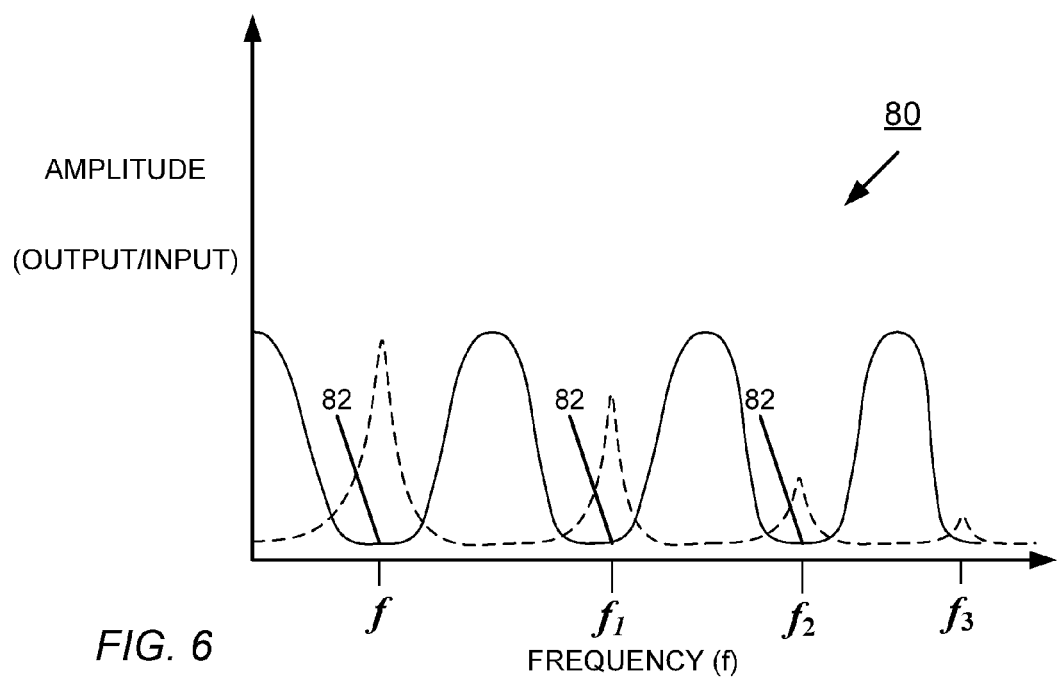
FIG. 6 is a plot of example frequencies introduced by the mixer into the solvent compositional stream overlaid against the plot of FIG. 4 showing the noise characteristic in the incoming solvent compositional stream.
Figure 7:
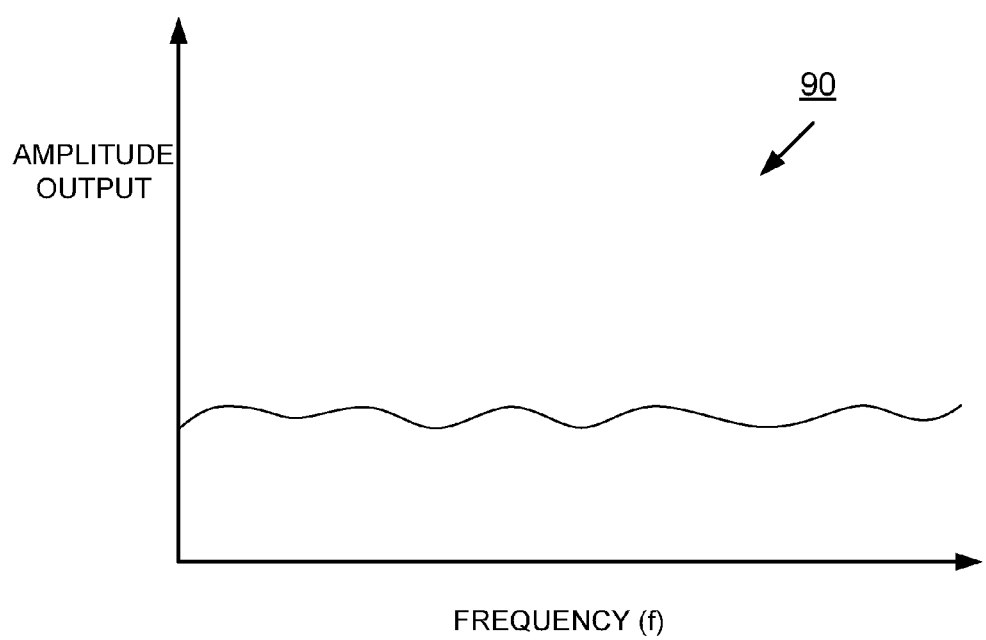
FIG. 7 is a plot showing the canceling effects of the frequencies introduced by the mixer upon the noise characteristic in incoming solvent compositional stream.

FIG. 6 shows a frequency-domain plot 80 in which the designed constituent frequencies associated with the mixing profile (solid lines) produced by the mixer 14 is superimposed on the example noise profile (dashed lines) described in connection with FIG. 4. The troughs 82 of the mixing profile are designed to coincide with the component and harmonic frequencies of the noise profile in order to produce an output compositional stream with such periodic error being attenuated or canceled, as illustrated in the frequency domain plot 90 FIG. 7.

Figure 8:
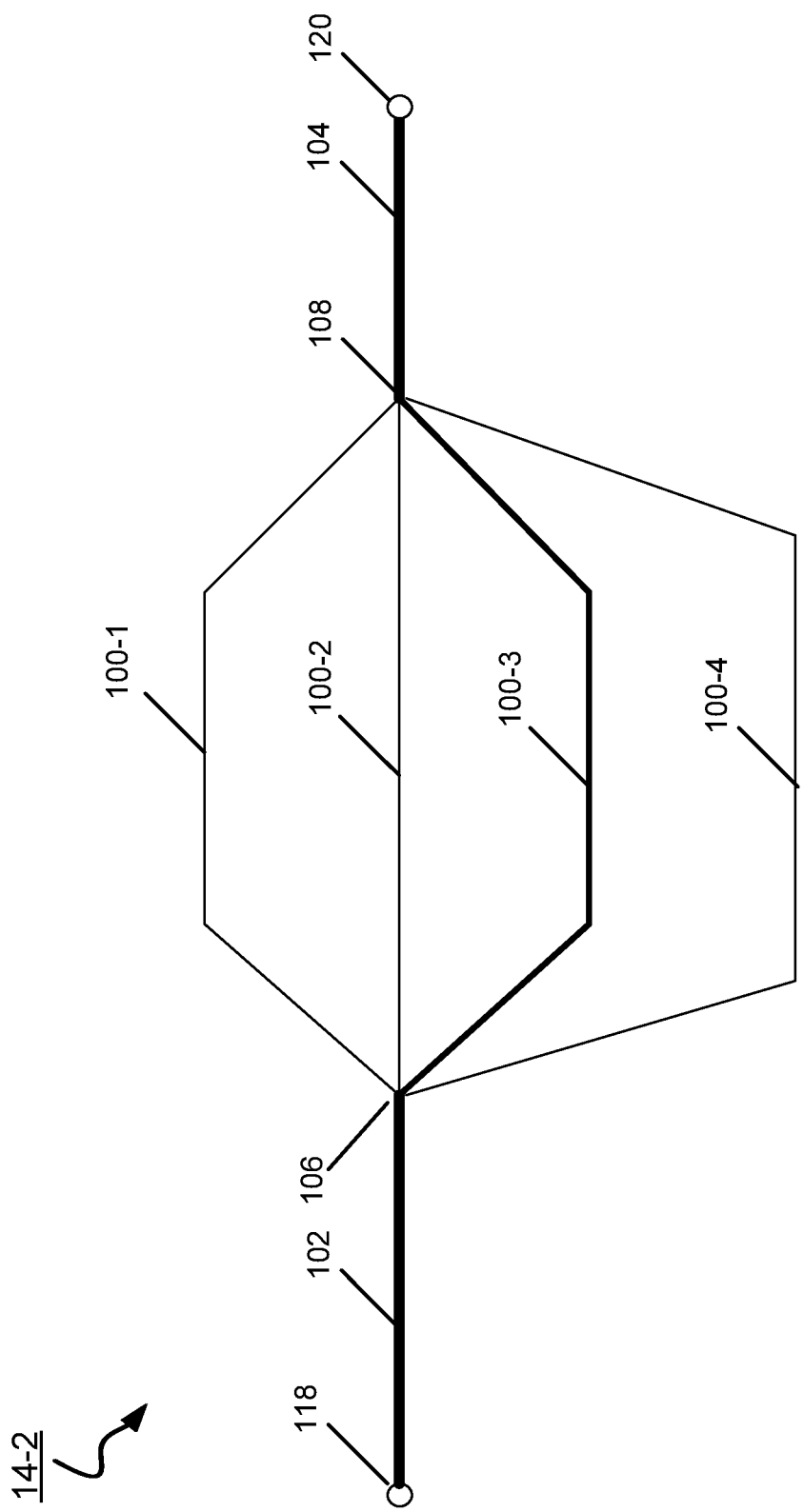
FIG. 8 is a diagram of another embodiment of a discrete path mixer.

FIG. 8 shows another example embodiment of a discrete path mixer 14-2, with an objective of illustrating that the principles described herein apply readily to other mixer designs. This discrete path mixer 14-2 has an intake port 118, an outlet port 120, and four microfluidic paths 100-1, 100-2, 100-3, and 100-4 (generally, 100) by which a compositional stream arriving at the intake port 118 can divide and pass to the outlet port 120. An inlet channel 102 extends from the intake port 118 to a distribution well 106. An outlet channel 104 extends from a mixing well 108 to the outlet port 120. Each path 100 starts at the distribution well 106 and ends at the mixing well 108.

In this example, the path 100-3 has a greater cross-sectional area (signified by line thickness) and correspondingly a lower flow resistance than the other paths 100-1, 100-2, 100-4; path 100-4 is the longest path, path 100-2 is the shortest path, and paths 100-1, 100-3 are approximately equal to each other in length. Although these two paths are 100-1, 100-3 approximately equal in length, the travel time for a compositional stream through path 100-1 is greater than through path 100-3 because of the differences in their cross-sectional areas.

The geometries of these paths 100 are tuned to produce a set of different dwell volumes that cooperatively produce a canceling or attenuating effect on a known noise characteristic in the incoming solvent compositional stream. This solvent compositional stream enters the intake port 118, travels the inlet channel 102, and splits at the distribution well 106 into four streams corresponding to the four paths 100. Each path carries a percentage of the incoming solvent compositional stream in accordance with its dwell volume. The four streams arrive at the mixing well 108 in accordance with the percentages carried by the paths 100 and recombine to produce an output compositional stream. The mixing profile achieved by these particular mixing percentages operate to attenuate or cancel the frequency, or band of frequencies, targeted specifically by the design of the mixer.

Figure 9:
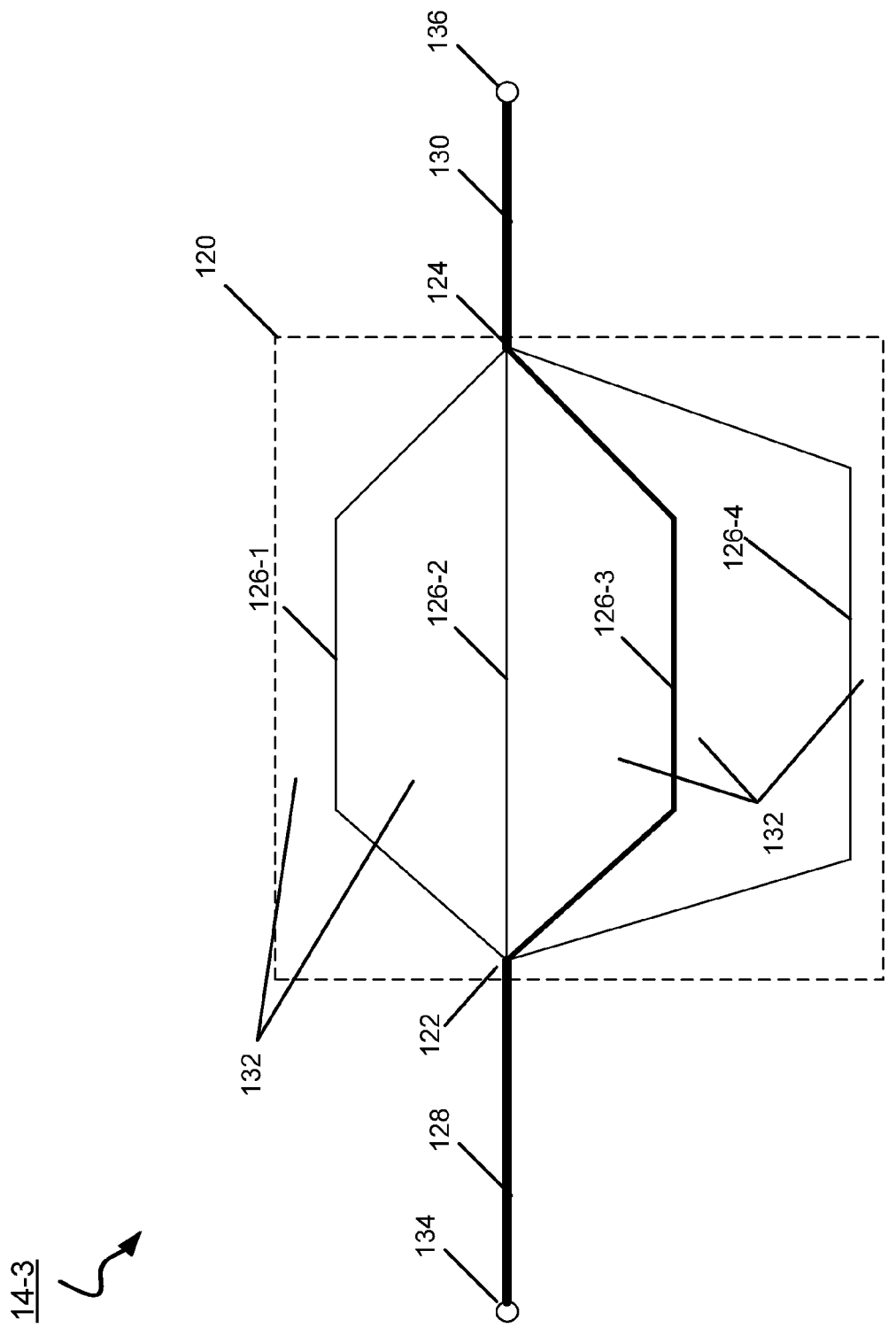
FIG. 9 is a diagram of another embodiment of a multi-path mixer referred to as a contoured surface mixer.

FIG. 9 shows another embodiment of multi-path mixer 14-3, referred to as a contoured surface mixer. The mixer 14-3 includes a contour surface chamber created by diffusion bonding or with a gasket. The contoured surface mixer has an inlet port 134, an outlet port 136, and a contoured region 120 between a distribution well 122 and a mixing well 124. The contoured region 120 has four major paths 126-1, 126-2, 126-3, and 126-4 (generally, 126). For purposes of facilitating comparisons between discrete path mixers and contoured surface mixers, the geometries of these paths 126 are similar to those paths 100 of the discrete mixer 14-2 of FIG. 8 (i.e., the geometries of path 126-1 are like path 100-1; those of path 126-2 are like path 126-2, etc.). An inlet channel 128 extends from the intake port 134 to the distribution well 122. An outlet channel 130 extends from the mixing well 124 to the outlet port 136. Each path 126 starts at the distribution well 122 and ends at the mixing well 124.

Each path 126 is bounded on both sides by contoured regions 132. By means of analogy, each path 126 passing between contoured regions 132 is like a river flowing through a valley, the valley floor sloping upwards from banks on both sides of each river. The valleys can have different depths and widths, and any given valley can itself have a varying depth and width. Neighboring valleys sharing a single contoured region 132 meet at a ridgeline 140 (i.e., a ridge that extends from the distribution well 122 to the mixing well 124 and defines the highest elevation between the valleys).

To continue with the analogy, each valley is like a floodplain. An incoming solvent compositional stream arriving at the distribution well 122 initially splits into four streams corresponding to the four paths 126. If the volume of the incoming compositional stream exceeds the capacity of a path, the banks of that path overflow, and the compositional stream begins to fill the valley through which that path passes. Advantageously, the valley provides additional area in which to mix solvents in the compositional stream. In addition, the capacity of a given valley may be exceeded, and the compositional stream can overflow a ridgeline of the valley and flow into a neighboring valley. In some embodiments, a covering surface of the chamber contacts one or more of the ridgelines 140 and operates to isolate neighboring valleys fluidically from each other so that fluid cannot overflow from one valley into the next.

Figure 10:
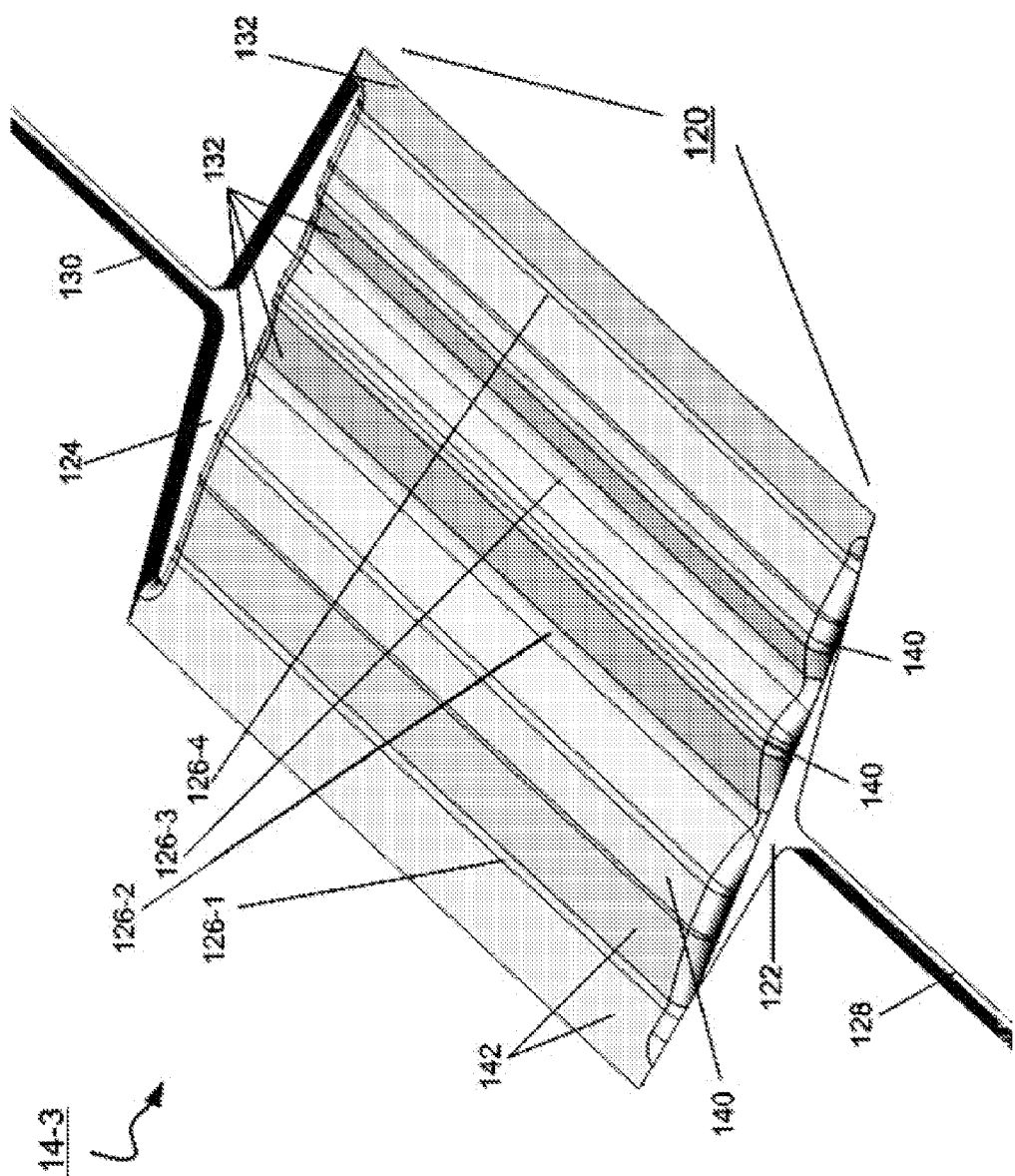
FIG. 10 is a top three-dimensional view of an embodiment of a contoured surface mixer.

FIG. 10 shows a three-dimensional view of an embodiment of the contoured surface mixer 14-3 (omitting a top layer or covering of the chamber to show the various underlying features of the contour region 120). The distribution well 122 and mixing well 124 are sunken regions at opposite ends of the mixer 14-3. Each path 126 extends from the distribution well 122 to the mixing well 124, bounded on both sides by upwardly sloping banks 142. A ridge 140 separates neighboring valleys.

The geometries of the paths and valleys can be designed to target specific noise profiles. The geometries of the paths 126 passing through the contour region 120, their width and depth, determine the primary characteristics of the mixer 14-3. The geometries of the secondary features of the contour region, such as the depth and width of the valleys, operate to smoothen or blend the primary characteristics produced by paths. The dwell volumes of the valleys (which include the paths that run through them) determine the mixing percentages at the mixing well 124.

Figure 11:
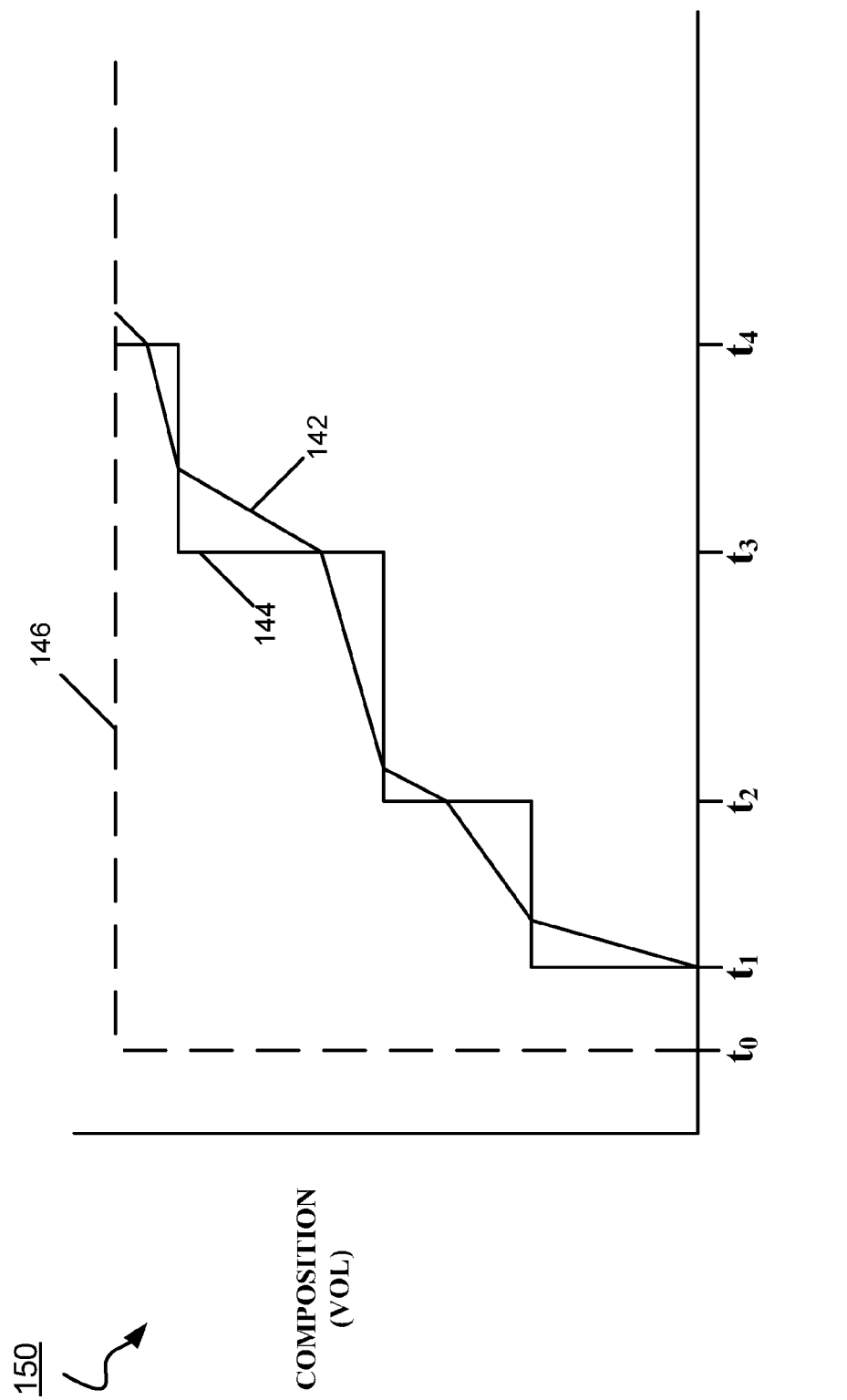
FIG. 11 is a plot comparing example output volumes produced over time by the contoured surface mixer and a similar discrete path mixer.

FIG. 11 shows a plot 150 of an example mixer output 142 produced by the four-path contoured surface mixer 14-3 of FIG. 9, compared to an example mixer output 144 of a similar discrete path mixer 14-2 of FIG. 8. The mixer input 146 (to both types of multi-path mixers) is represented as a step that enters the mixer at time $t_0$. The mixer output 144 of the discrete path mixer 14-2 has four distinct steps that coincide with the travel time of each portion of the compositional step through each of the four paths 100. The mixer output 142 of the four-path contoured surface mixer 14-3 has four corresponding steps, which are less sharp than the steps of the mixer output 144. As shown, an input step of composition sent through the contoured surface mixer 14-3 comes out as several blended steps. Accordingly, the contoured surface of the contoured surface mixer 14-3 can achieve a more analog-like filter effect for canceling noise than the discrete path mixer 14-2.

Figure 12:
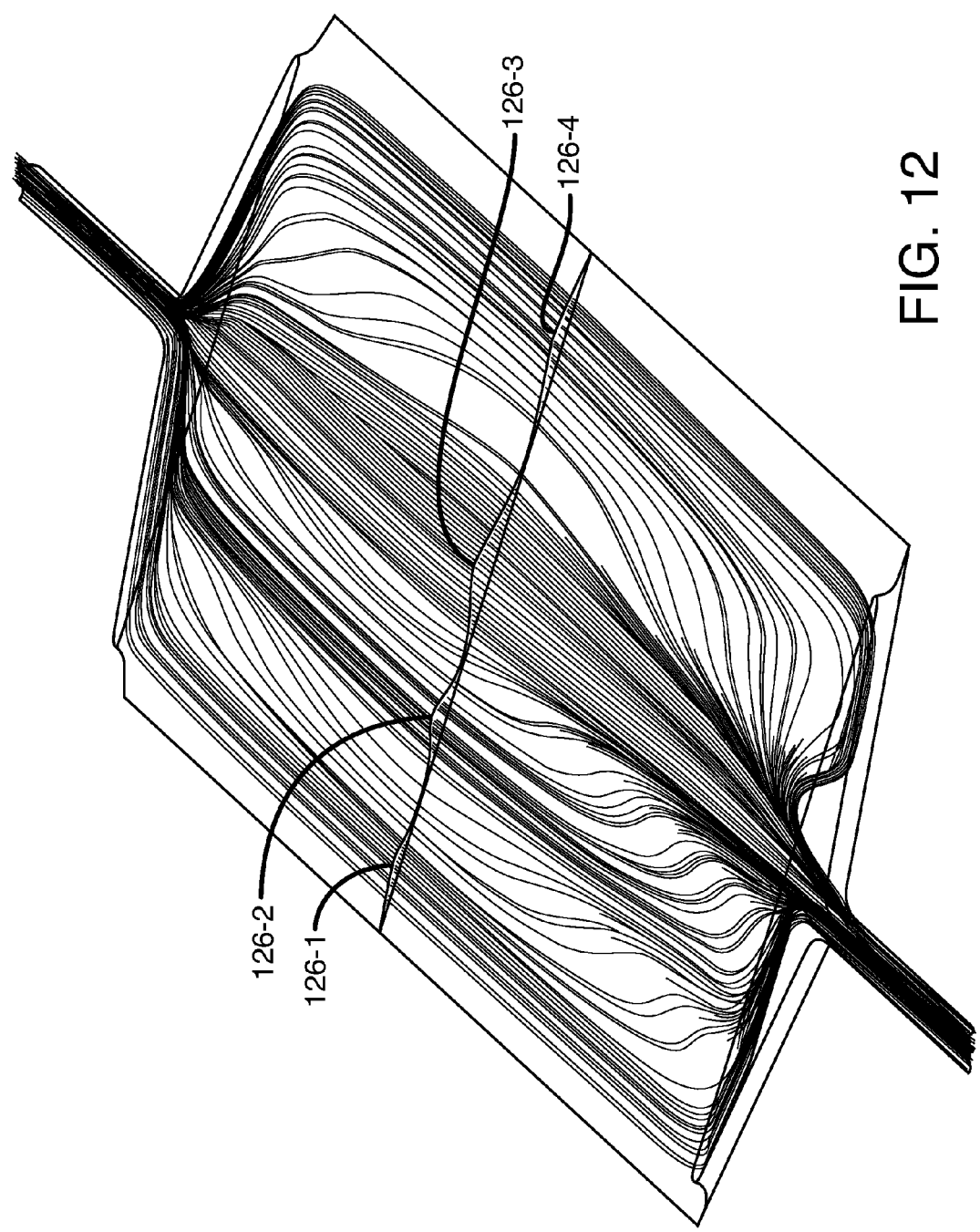
FIG. 12 is a diagram showing an example of time spent by fluid taking the different paths through a contoured surface mixer.

FIG. 12 is a diagram illustrating the different streams of composition flowing through the contoured surface mixer 14-3 of FIG. 10. Peak volumes run predominantly through the paths 126-1, 126-2, 126-3, 126-4; some of the composition can overflow the banks of some or all of the paths (e.g., 126-1), and spill over into neighboring valleys. In general, fluid spends less time in those paths 126-2, 126-3 directly opposite the inlet channel 128, and more time in the outer paths 126-1, 126-4.

While the invention has been shown and described with reference to specific preferred embodiments, it should be understood by those skilled in the art that various changes in form and detail may be made therein without departing from the spirit and scope of the invention as defined by the following claims.

What is claimed is:

1. A method of mixing a solvent composition for a microfluidic separation system, comprising:
   providing a mixing well;
   providing a distribution well;
   receiving an incoming flow of the solvent composition, including an input compositional step having a set volume, a known noise characteristic, constituent frequencies, and a noise profile, into the distribution well; and
   providing at least three fluidic paths extending from the distribution well to the mixing well, the flow of solvent composition being split at the distribution well into as many streams as fluidic paths, the fluidic paths having different dwell volumes that determine a percentage of the flow of solvent composition carried by each of the fluidic paths, the fluidic paths configured to produce output steps of the streams to produce a mixing profile having designed constituent frequencies to target the constituent frequencies the known noise characteristic in the flow of solvent composition, the output steps of the streams recombining at the mixing well in accordance with percentages of the input compositional step determined by the dwell volumes of the fluidic paths and respectively different predetermined travel times to produce an output compositional stream for the microfluidic separation system having the known noise characteristic attenuated, wherein the designed constituent frequencies of the mixing profile attenuate the constituent frequencies and target the noise profile.

2. The method of claim 1, wherein the fluidic paths have different lengths.

3. The method of claim 1, wherein the fluidic paths have different cross-sectional areas.

4. The method of claim 1, wherein the dwell volume of a given fluidic path is a function of length and cross-sectional area of the given fluidic path.

5. The method of claim 1, wherein the known noise characteristic is produced by a low-pressure gradient pump system that provides the flow of solvent composition.

6. The method of claim 1, wherein the known noise characteristic is produced deliberately by a high-pressure gradient pump system that provides the flow of solvent composition.

7. A method of mixing a solvent composition, comprising:
providing a pump system pumping a flow of solvent composition with a known noise characteristic;
providing a mixer with a mixing well;
providing a distribution well;
receiving the flow of solvent composition including an input compositional step having a set volume, the known noise characteristic, constituent frequencies, and a noise profile; and
providing a plurality of fluidic paths extending from the distribution well to the mixing well, the flow of solvent composition being split at the distribution well into as many streams as fluidic paths, the fluidic paths having different dwell volumes that determine a percentage of the flow of solvent composition carried by each of the fluidic paths, the fluidic paths configured to produce output steps of the streams to produce a mixing profile having designed constituent frequencies to target the constituent frequencies of the known noise characteristic in the flow of solvent composition, the output steps of the streams recombining at the mixing well in accordance with percentages of the input compositional step determined by the dwell volumes of the fluidic paths and respectively different predetermined travel times to produce an output compositional stream for the microfluidic separation system having the known noise characteristic attenuated, wherein the designed constituent frequencies of the mixing profile attenuate the constituent frequencies and target the noise profile.

8. The method of claim 7, wherein the fluidic paths have different lengths.

9. The method of claim 7, wherein the fluidic paths have different cross-sectional areas.

10. The method of claim 7, wherein the dwell volume of a given fluidic path is a function of a length and cross-sectional area of the given fluidic path.

11. The method of claim 7, wherein the pump system is a low-pressure gradient pump system that produces the known noise characteristic.

12. The method of claim 7, wherein the pump system is a high-pressure gradient pump system deliberately operated to produce the known noise characteristic.

13. A mixer for a microfluidic separation system, comprising:
a mixing well;
a distribution well for receiving an incoming flow of solvent composition; and
a contoured surface disposed between the distribution and mixing wells, the contoured surface having a plurality of fluidic paths extending from the distribution well to the mixing well, each fluidic path passing through a different valley defined by opposing upwardly sloping banks, the incoming flow of solvent composition splitting at the distribution well into as many streams as fluidic paths, the streams recombining at the mixing well to produce an output compositional stream, wherein neighboring valleys abut at a ridgeline traversable by the solvent composition.

14. The mixer of claim 13, wherein each valley has a dwell volume that determines a percentage of the flow of solvent composition that passes through that valley.

15. The mixer of claim 14, wherein the dwell volumes of the valleys are specifically configured to target a known noise characteristic in the flow of solvent composition.

16. The mixer of claim 14, wherein the streams recombine at the mixing well in accordance with the percentages determined by the dwell volumes of the valleys to produce an output compositional stream with the noise characteristic attenuated.

17. The mixer of claim 14, wherein the dwell volume of a given valley is a function of length and width of the valley and of a dwell volume of the fluidic path extending through that given valley.

18. The mixer of claim 13, wherein the fluidic paths have different lengths.

19. The mixer of claim 13, wherein the fluidic paths have different cross-sectional areas.

20. The mixer of claim 13, wherein neighboring valleys are fluidically isolated from each other.

21. A microfluidic system, comprising:
a pump system pumping a flow of solvent composition; and
a mixer with a distribution well for receiving the flow of solvent composition, a mixing well, and a contoured surface disposed between the distribution and mixing wells, the contoured surface having a plurality of fluidic paths extending from the distribution well to the mixing well, each fluidic path passing through a different valley defined by opposing upwardly sloping banks, the flow of solvent composition splitting at the distribution well into as many streams as fluidic paths, the streams recombining at the mixing well to produce an output compositional stream, wherein neighboring valleys abut at a ridgeline traversable by the solvent composition.

22. The microfluidic system of claim 21, wherein each valley has a dwell volume that determines a percentage of the flow of solvent composition that passes through that valley.

23. The microfluidic system of claim 22, wherein the dwell volumes of the valleys are specifically configured to target a known noise characteristic in the flow of solvent composition.

24. The microfluidic system of claim 22, wherein the streams recombine at the mixing well in accordance with the percentages determined by the dwell volumes of the valleys to produce an output compositional stream with the noise characteristic attenuated.

25. The microfluidic system of claim 22, wherein the dwell volume of a given valley is a function of length and width of the valley and of a dwell volume of the fluidic path extending through that given valley.

26. The microfluidic system of claim 21, wherein the fluidic paths have equal lengths.

27. The microfluidic system of claim 21, wherein the fluidic paths have different cross-sectional areas.

28. The microfluidic system of claim 21, wherein neighboring valleys are fluidically isolated from each other.

* * * * *